United States Patent
Hong et al.

(10) Patent No.: US 12,274,785 B2
(45) Date of Patent: Apr. 15, 2025

(54) SUSTAINED-RELEASE PHARMACEUTICAL COMPOSITIONS COMPRISING AN IMMUNOMODULATING AGENT AND USES THEREOF

(71) Applicants: TAIWAN LIPOSOME CO., LTD., Taipei (TW); TLC BIOPHARMACEUTICALS, INC., South San Francisco, CA (US)

(72) Inventors: Keelung Hong, South San Francisco, CA (US); Walter Gwathney, South San Francisco, CA (US); Jonathan Fang, South San Francisco, CA (US); Hao-Wen Kao, South San Francisco, CA (US); Yi-Yu Lin, South San Francisco, CA (US)

(73) Assignees: TAIWAN LIPOSOME CO., LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 794 days.

(21) Appl. No.: 17/285,623

(22) PCT Filed: Oct. 15, 2019

(86) PCT No.: PCT/US2019/056186
§ 371 (c)(1),
(2) Date: Apr. 15, 2021

(87) PCT Pub. No.: WO2020/081485
PCT Pub. Date: Apr. 23, 2020

(65) Prior Publication Data
US 2021/0393524 A1 Dec. 23, 2021

Related U.S. Application Data

(60) Provisional application No. 62/746,810, filed on Oct. 17, 2018.

(51) Int. Cl.
| | | |
|---|---|---|
| *A61K 9/127* | (2006.01) | |
| *A61K 9/1273* | (2025.01) | |
| *A61K 31/137* | (2006.01) | |
| *A61K 31/4245* | (2006.01) | |
| *A61K 47/02* | (2006.01) | |
| *A61K 47/24* | (2006.01) | |
| *A61K 47/26* | (2006.01) | |
| *A61K 47/28* | (2006.01) | |
| *A61K 47/36* | (2006.01) | |

(52) U.S. Cl.
CPC ............ *A61K 9/127* (2013.01); *A61K 9/1273* (2013.01); *A61K 31/137* (2013.01); *A61K 31/4245* (2013.01); *A61K 47/02* (2013.01); *A61K 47/24* (2013.01); *A61K 47/26* (2013.01); *A61K 47/28* (2013.01); *A61K 47/36* (2013.01)

(58) Field of Classification Search
CPC .... A61K 9/127; A61K 9/1273; A61K 31/137; A61K 31/4245; A61K 47/02; A61K 47/24; A61K 47/26; A61K 47/28; A61K 47/36
See application file for complete search history.

(56) References Cited

U.S. PATENT DOCUMENTS

| | | |
|---|---|---|
| 5,192,549 A | 3/1993 | Barenolz et al. |
| 2014/0271822 A1 | 9/2014 | McGhee et al. |
| 2015/0157610 A1* | 6/2015 | Minamino ............... A61P 29/00 514/291 |
| 2016/0030340 A1 | 2/2016 | Kan et al. |
| 2017/0071858 A1 | 3/2017 | Hong et al. |

FOREIGN PATENT DOCUMENTS

| | | | |
|---|---|---|---|
| CN | 101199505 A * | 6/2008 | |
| CN | 101601654 A | 12/2009 | |
| CN | 101756902 A | 6/2010 | |
| CN | 102406606 A | 4/2012 | |
| CN | 108354904 A | 8/2018 | |
| JP | 2016513655 A | 5/2016 | |
| JP | 2016518340 A | 6/2016 | |
| WO | WO-2016022549 A1 * | 2/2016 | ........... A61K 31/337 |
| WO | 2016191547 A1 | 12/2016 | |
| WO | 2017123588 A1 | 7/2017 | |
| WO | WO-2017120537 A1 * | 7/2017 | ........... A61K 31/337 |
| WO | 2019082139 A1 | 5/2019 | |
| WO | 2020023445 A1 | 1/2020 | |

OTHER PUBLICATIONS

Arthritis & Rheumatism vol. 58, No. 1, Jan. 2008, pp. 119-129 DOI 10.1002/art.23230. Avnir et al. Amphipathic Weak Acid Glucocorticoid Prodrugs, Jan. 2008 (Year: 2008).*
Journal of Controlled Release 160 (2012) 299-305; Glucocorticoids in nano-liposomes administered intravenously and subcutaneously to adjuvant arthritis rats are superior to the free drugs in suppressing arthritis and inflammatory cytokines; Ulmansky et al. (Year: 2012).*
El-Mezayen et al.; Hepatic stellate cell-targeted imatinib nanomedicine versus conventional imatinib: A novel strategy with potent efficacy in experimental liver fibrosis; Elsevier; JCR (Journal of Controlled Release), 266 (2017) 226-237 (Year: 2017).*

(Continued)

*Primary Examiner* — Robert A Wax
*Assistant Examiner* — John W Lippert, III
(74) *Attorney, Agent, or Firm* — Pilloff Passino & Cosenza LLP; Rachel Pilloff; Sean Passino

(57) ABSTRACT

The present invention relates to a pharmaceutical composition comprising at least one liposome and a therapeutic agent for treating an auto-immune disease with a high therapeutic agent to lipid ratio and a high encapsulation efficiency. The pharmaceutical composition improves the pharmacokinetic profile and sustains the release of the therapeutic agent. Also provided is the method for treating an auto-immune disease using the pharmaceutical composition disclosed herein.

8 Claims, 2 Drawing Sheets

(56) References Cited

OTHER PUBLICATIONS https://www.amazon.com/Lecithin-Hydrogenated-CAS-92128-87-5-Phospholipids/dp/B07XSC1ZSB?th=1; accessed Dec. 2023 (Year: 2023).*
Mao et al.; A novel liposomal formulation of FTY720 (Fingolimod) for promising enhanced targeted delivery; Elsevier; Nanomedicine: Nanotechnology, Biology, and Medicine 10 (2014) 393-400 (Year: 2014).*
Machine translation for CN101199505A (Year: 2008).*
https://medlineplus.gov/druginfo/meds/a611006.html#:~: text=Fingolimod%20is%20in%20a%20class,that%20may%20cause%20nerve%20damage. (accessed Jan. 2023) (Year: 2017).*
Office action for China Application No. 201980061938.5, mailed Feb. 9, 2023.
Office action for China Application No. 201980061938.5, mailed Jun. 27, 2023.
First Examination Report for India Application No. 202117017227, mailed Oct. 25, 2022.
Hearing Notice for India Application No. 202117017227, mailed Oct. 4, 2023.
Office Action for Japan Application No. 2021-521380, mailed Oct. 3, 2023.
Office Action for Taiwan Application No. 108136993, mailed Dec. 14, 2021.
Yicheng Mao et al., "A novel liposomal formulation of FTY720 (Fingolimod) for promising enhanced targeted delivery," Nanomedicine, Feb. 2014, pp. 393-400, vol. 10, No. 2.
Yuval Avnir et al., "Amphipathic weak acid glucocorticoid prodrugs remote-loaded into sterically stabilized nanoliposomes evaluated in arthritic rats and in a Beagle dog: A novel approach to treating autoimmune arthritis," Arthritis & Rheumatism, Jan. 2008, pp. 119-129, vol. 58, No. 1.
Rina Ulmansky et al., "Glucocorticoids in nano-liposomes administered intravenously and subcutaneously to adjuvant arthritis rats are superior to the free drugs in suppressing arthritis and inflammatory cytokines," Journal of Controlled Release, Jun. 10, 2012, pp. 299-305, vol. 160, No. 2.
International Search Report & Written Opinion for PCT/US2019/056186, mailed Jan. 2, 2020.
Office Action for related Taiwan application 108136993 (Filed Oct. 15, 2019), mailed Aug. 3, 2020.
Office Action for related Taiwan application 108136993 (Filed Oct. 15, 2019), mailed Jan. 11, 2021.
Daryl C. Drummond et al., "Improved Pharmacokinetics and Efficacy of a Highly Stable Nanoliposomal Vinorelbine," The Journal of Pharmacology and Experimental Therapeutics, Jan. 2009, pp. 321-330, vol. 328, No. 1.
Nesrine S. El-Mezayen et al., "Hepatic stellate cell-targeted imatinib nanomedicine versus conventional imatinib; A novel strategy with potent efficacy in experimental liver fibrosis." Journal of Controlled Release, Sep. 28, 2017, pp. 226-237, vol. 266.
Michael R. Mardiney et al., "The Immunosuppressive Effect of Amantadine Upon the Response of Lymphocytes To Specific Antigens In Vitro," Transplantation, Sep. 1971, pp. 183-188, vol. 12, No. 3.
Michael K. Robinson et al, "Immunosuppressive Effects of Clonidine on the Induction of Contact Sensitization in the Balb/c Mouse," Journal of Investigative Dermatology, Nov. 1990, pp. 587-591, vol. 95, No. 5.
G. V. Idova et al., "Effects of the Atypical Antipsychotic Quetiapine on the Immune Response in Aggressive Mice in a Model of Social Stress," Neuroscience and Behavioral Physiology, May 2018, pp. 506-510, vol. 48, No. 4.
Arnold Angelo M. Pineda et al., "Preventive and therapeutic effects of the selective Rho-kinase inhibitor fasudil on experimental autoimmune neuritis," Journal of Neurological Sciences, Mar. 18, 2011, pp. 115-120, vol. 306, No. 1.
Bernd Zanker et al., "The immunosuppressive effects of verapamil upon mitogen activated and allo-antigen inducible human cytotoxic t-lymphocytes," International Journal of Immunopharmacology, Jul. 1994, pp. 507-517, vol. 16, No. 7.
Ralf L. J. Schmidt et al., "Chloroquine inhibits human CD4+ T-cell activation by AP-1 signaling modulation," Scientific Reports, Mar. 2017, vol. 7, No. 1.
Paola Sacerdote et al: "Antinociceptive and immunosuppressive effects of opiate drugs: a structure-related activity study", British Journal of Pharmacology, Feb. 2009, pp. 834-840, vol. 121, No. 4.
Theresa Lowinus et al., "Immunomodulation by memantine in therapy of Alzheimer's disease is mediated through inhibition of Kv1.3 channels and T cell responsiveness," Oncotarget, Aug. 2016, pp. 53,797-53,807, vol. 7, No. 33.
Office Action for related Europe Application No. 19873971.6, mailed Jun. 13, 2022.
Office Action for related China Application No. 201980061938.5, mailed Jul. 15, 2022.
Ting Ho et al., "Research Development of ammonium sulfate gradient in liposome manufacture" China Pharmacist, Dec. 2009, pp. 1,723-1,725, vol. 12, No. 12.

* cited by examiner

SUSTAINED-RELEASE PHARMACEUTICAL COMPOSITIONS COMPRISING AN IMMUNOMODULATING AGENT AND USES THEREOF

CROSS-REFERENCE TO RELATED APPLICATION

This application claims the benefit of U.S. Application No. 62/746,810, filed on 17 Oct. 2018, the entire disclosure of which is incorporated herein by reference.

TECHNICAL FIELD

The present invention is directed to a sustained-release pharmaceutical composition comprising an immunomodulating agent with a high drug to lipid ratio and a high encapsulation efficiency using at least one trapping agent. The high drug to lipid ratio, high encapsulation efficiency and sustained release profile of the claimed pharmaceutical composition reduce the frequency of drug administration, increase patient compliance and improve the therapeutic outcome.

BACKGROUND

Sphingosine-1-phosphate (S 1P) receptor agonists, such as fingolimod, have been approved for treatment of auto-immune diseases, such as multiple sclerosis, including the relapsing forms of multiple sclerosis (RMS), S1P receptor agonists are administered orally and a major concern is the agonism of the S1P receptor may lead to bradycardia. In view of this potentially fatal cardiac event, patients who receive their first dose of fingolimod are monitored by a health care professional for at least 6 hours after dosing (GILENYA® (fingolimod) package insert). Developing a formulation to minimize the adverse cardiac event, improve drug tolerability and mitigate the need of dose titration would be beneficial. Furthermore, an extended release formulation to reduce the dose or dosing frequency of S1P receptor agonists would be advantageous.

Liposomes as a drug delivery system is a successful technology and has been widely used for developing sustained-release formulations for various drugs. Drug loading into liposomes can be attained either passively (the drug is encapsulated during liposome formation) or remotely/actively (creating a transmembrane pH- or ion-gradient during liposome formation and followed by loading the drug by the driving force generated from the gradients after liposome formation), see U.S. Pat. Nos. 5,192,549 and 5,939,096. Although the general method of drug loading into liposomes is well documented in the literature, only a handful of therapeutic agents were loaded into liposomes with high encapsulation efficiency. Numerous factors can affect the encapsulation efficiency of liposomes, including but not limited to, the physical and chemical properties of the therapeutic agent, for example, hydrophilic/hydrophobic characteristics, dissociation constant, solubility and partition coefficient, lipid composition, trapping agent, reaction solvent, and particle size (Proc. Natl. Acad. Sci U S A. 2014; 111(6): 2283-2288 and Drug Metab. Dispos. 2015; 43 (8):1236-45).

Mao et al. discloses a liposomal fingolimod formulation including egg phosphatidylcholine, cholesterol, and DSPE-PEG2000 (Nanomed. 2014; 10(2): 393-400) using the passive loading method and the solvent injection method. The liposomes were 157.5 nm in diameter with an encapsulation efficiency of 85.2%, and a final drug to lipid ratio (D/L) of 0.11. Unfortunately, passive loading limits the amount of drug that can be encapsulated in liposome.

There remains an unmet need for a sustained release formulation with a high drug to lipid ratio and high encapsulation efficiency to reduce dosing frequency of immunomodulating agents and improve therapeutic outcome. The present invention addresses this need and other needs.

SUMMARY OF THE INVENTION

In one embodiment, a sustained release pharmaceutical composition comprises (a) at least one liposome comprising a bilayer membrane; (b) a trapping agent; and (c) an immunomodulating agent, wherein the bilayer membrane comprises at least one lipid and the molar ratio of the immunomodulating agent to the lipid is higher than or equal to about 0.2 is provided.

According to another embodiment of the present invention, methods are provided for treating an auto-immune disease, comprising the steps of administering a pharmaceutical composition described herein to a subject in need thereof.

Also provided are the uses of the pharmaceutical composition described herein in the manufacture of a medicament for treating an auto-immune disease.

Further provided is a medicament for treating an auto-immune disease in a subject, comprising a therapeutically effective amount of the pharmaceutical composition described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below.

Embodiments of the invention covered by this patent are defined by the claims below, not this summary This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

A further understanding of the nature and advantages of the present invention may be realized by reference to the remaining portions of the specification and the drawings.

DETAILED DESCRIPTION OF THE INVENTION

Figure 1:
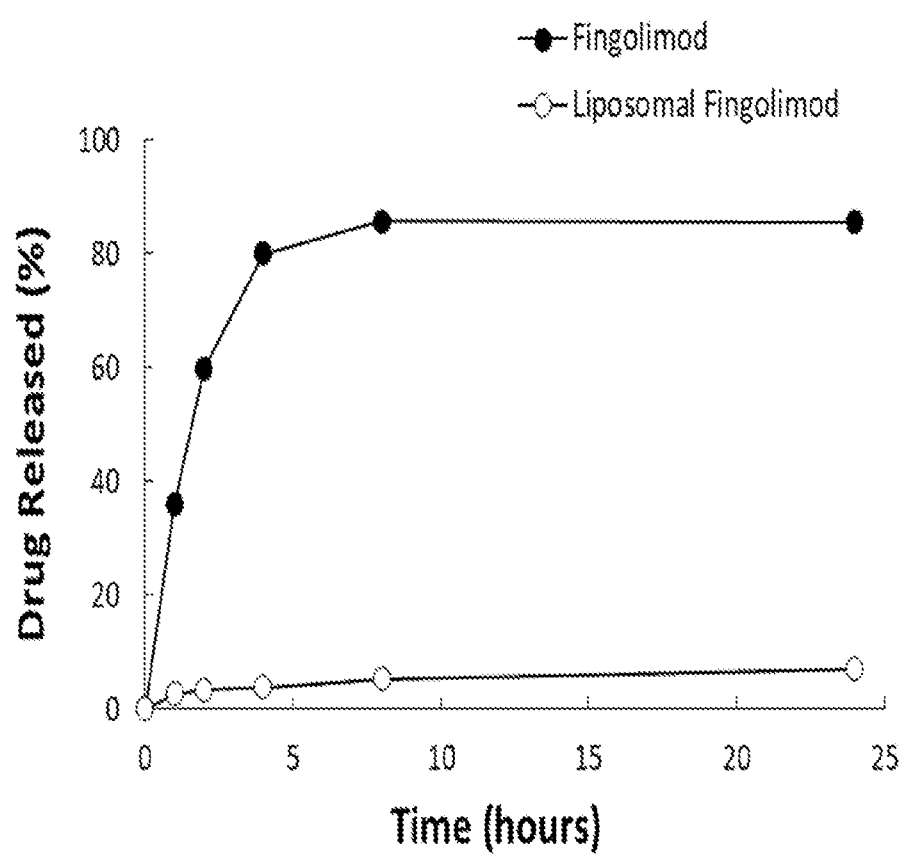
FIG. 1 is a line graph showing the in vitro release profile of the liposomal fingolimod formulation of Example 1 and free fingolimod.
Figure 2:
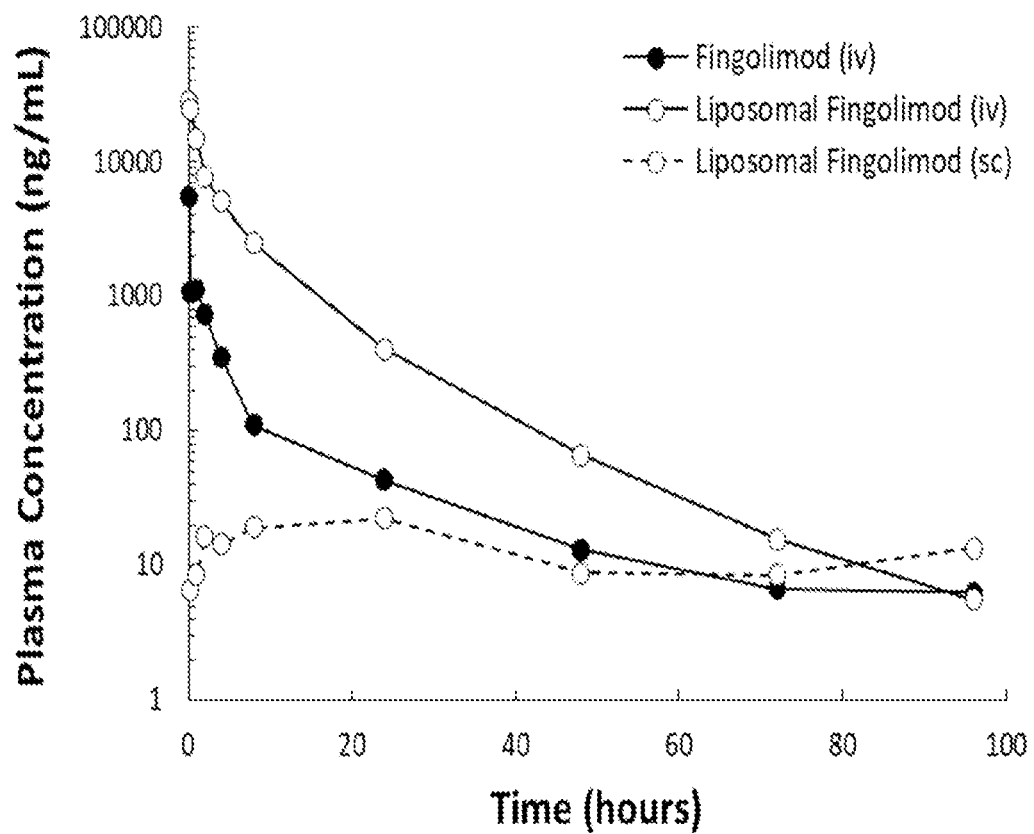
FIG. 2 is a line graph showing the plasma fingolimod concentration in rats after intravenous injection of free or liposomal fingolimod formulation and subcutaneous injection of liposomal fingolimod formulation.

As employed above and throughout the disclosure, the following terms, unless otherwise herein, the singular forms "a", "an" and "the" include the plural reference unless the context clearly indicates otherwise.

All numbers herein may be understood as modified by "about." As used herein, the term "about" refers to a range of ±10% of a specified value.

An "effective amount," as used herein, refers to a dose of the pharmaceutical composition to elicit an immunomodulating effect, such as reducing the symptoms and/or signs of an auto-immune disease. The term "effective amount" and "therapeutically effective amount" are used interchangeably.

The terms "immunomodulating agent" and "a therapeutic agent for treating an auto-immune disease" are used interchangeably and refer to a therapeutic agent that elicit an immunomodulating effect to reduce the symptoms and/or signs of an autoimmune disease.

The term "treating," "treated," or "treatment" as used herein includes preventative (e.g. prophylactic), palliative, and curative methods, uses or results. The terms "treatment" or "treatments" can also refer to compositions or medicaments. Throughout this application, by treating is meant a method of reducing or delaying one or more symptoms or signs of an auto-immune disease or the complete amelioration of an auto-immune disease as detected by art-known techniques. Art recognized methods are available to evaluate an auto-immune disease and its symptoms, including but not limited to, erythrocyte sedimentation rate, C-reactive protein concentration, anti-cyclic citrullinated peptide antibody, anti-nuclear antibody, and X-rays. Thus, the reduction can be about 1, 5, 10, 20, 30, 40, 50, 60, 70, 80, 90, 100%, or any amount of reduction in between.

The term "auto-immune disease," as used herein, is a group of diseases, which include, but not limited to, Hashimoto's thyroiditis rheumatoid arthritis, systemic and cutaneous forms of lupus erythematosus, ulcerative colitis and multiple sclerosis, where individual's immune system recognizes itself as a foreign body and causes loss of function or destruction of normal tissue through humoral or cellular immune responses to the body's own tissue constituents. In one embodiment, the auto-immune disease is systemic, such as systemic lupus erythematosus. In another embodiment, the auto-immune is localized or organ specific, such as thyroiditis.

The term "subject" can refer to a vertebrate having or suspect of having an auto-immune disease. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Liposome

The terms "liposome", "liposomal" and related terms as used herein are characterized by an interior aqueous space sequestered from an outer medium by one or more bilayer membranes forming a vesicle. In certain embodiments, the interior aqueous space of the liposome is substantially free of a neutral lipid, such as triglyceride, non-aqueous phase (oil phase), water-oil emulsions or other mixtures containing non-aqueous phase. Non-limiting examples of liposomes include small unilamellar vesicles (SUV), large unilamellar vesicles (LUV), and multi-lamellar vesicles (MLU) with an average diameter ranges from 50-20 μm, 50-450 nm, 50-400 nm, 50-350 nm, 50-300 nm, 50-250 nm, 50-200 nm, 100-500 nm, 100-450 nm, 100-400 nm, 100-350 nm, 100-300 nm, 100-250 nm or 100-200 nm.

Bilayer membranes of liposomes are typically formed by at least one lipid, i.e. amphiphilic molecules of synthetic or natural origin that comprise spatially separated hydrophobic and hydrophilic domains. Examples of lipid, including but not limited to, dialiphatic chain lipids, such as phospholipids, diglycerides, dialiphatic glycolipids, single lipids such as sphingomyelin and glycosphingolipid, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1' -rac-glycerol) (sodium salt) (PSPG), 1,2-distearoyl-sn-glycero-3-phospho-(1' -rac-glycerol) (sodium salt) (DSPG), 1,2-dioleoyl-sn-glycero-3-phospho-(1' -rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanolamine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanolamine (PEG-DSPE), 1,2-dioleoyl-sn-glycero-3-phosphoethanolamine (DOPE), 1,2-dipalmitoyl-sn-glycero-3-phospho-(1' -myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). In some embodiments, the lipid is a lipid mixture of one or more of the foregoing lipids, or mixtures of one or more of the foregoing lipids with one or more other lipids not listed above, membrane stabilizers or antioxidants.

In certain embodiments, the mole percent of the lipid in the bilayer membrane of the liposome is about 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45 or any value or range of values therebetween (e.g., about 45-80%, about 45-75%, about 45-70%, about 45-65%, about 50-80%, about 50-75%, about 50-70% or about 50-65%).

In some embodiments, the lipid comprises a mixture of a first lipid and a second lipid. In some embodiments, the first lipid is selected from the group consisting essentially of phosphatidylcholine (PC), HSPC, DSPC, DPPC, DMPC, PSPC and combination thereof and the second lipid is selected from the group consisting essentially of a phosphatidylethanolamine, phosphatidylglycerol, PEG-DSPE, DPPG and combination thereof. In other embodiments, the mole percent of the first lipid in the liposome is equal or less than about 79.9, 79.5, 79.1, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40 or any value or range of values therebetween (e.g., about 40-79.9%, about 40-79.5%, about 40-79.1%, about 40-75%, about 40-70%, about 40-65%, about 45-79.9%, about 45-79.5%, about 45-79.1%, about 45-75%, about 45-70%, about 45-65%, about 45-60%, about 50-79.9%, about 50-79.5%, about 50-79.1%, about 50-75%, about 50-70%, about 50-65% or about 50-60%) and the mole percent of the second lipid in the liposome is equal to or less than about 10, 9, 8, 7, 6, 5, 4, 3, 2, 1, 0.5, 0.1 or any value or range of values therebetween (e.g., about 0.1-10%, about 0.1-9%, about 0.1-8%, about 0.1-7%, about 0.1-6%, about 0.1-5%, about 0.5-10%, about 0.5-9%, about 0.5-8%, about 0.5-7%, about 0.5-6% or about 0.5-5%).

Bilayer membranes of liposomes further comprise less than about 55 mole percentage of steroids, preferably cholesterol. In certain embodiments, the % of the steroid (such as cholesterol) in the bilayer membrane is about 20-55%, about 20-50%, about 20-45%, about 20-40%, about 25-55%, about 25-50%, about 25-45% or about 25-40%.

In one exemplary embodiment, the mole % of the lipid and cholesterol in the bilayer membrane of the liposome is about 45-80%: 20-55% or 50-75%: 25-50%. In another exemplary embodiment, the mole % of the first lipid, the second lipid and cholesterol in the bilayer membrane is about 40-79.5%: 0.5-10%: 20-55%, 40-79.9%: 0.1%-10%: 20-55%, 40-75%: 0.1-10%: 20-50% or 45-70%: 0.1-10%: 25-45%, and the first lipid is HSPC, DMPC, DPPC, DSPC or combination thereof and the second lipid is DSPE-PEG2000, DPPG or combination thereof.

Remote Loading

The term "remote loading" as used herein is a drug loading method which involves a procedure to transfer a therapeutic agent from the external medium across the bilayer membrane of the liposome to the interior aqueous space by a polyatomic ion-gradient. Such gradient is generated by encapsulating at least one polyatomic ion as a trapping agent in the interior aqueous space of the liposome and replacing the outer medium of the liposome with an external medium with a lower polyatomic ion concentration, for example, pure water, sucrose solution and saline, by known techniques, such as column separation, dialysis or centrifugation. A polyatomic ion gradient is created between the interior aqueous space and the external medium of the liposomes to trap the therapeutic agent in the interior aqueous space of the liposomes. Exemplary polyatomic ion as trapping agents include, but are not limited to, sulfate, sulfite, phosphate, hydrogen phosphate, molybdate, carbonate and nitrate. Exemplary trapping agents include, but are not limited to, ammonium sulfate, ammonium phosphate, ammonium molybdate, ammonium sucrose octasulfate, triethylammonium sucrose octasulfate and dextran sulfate.

In an embodiment, the concentration of ammonium sulfate is about 100 to about 600 mM, about 150 to about 500 mM or about 200 to about 400 mM. In another embodiment, the concentration of triethylammonium sucrose octasulfate is about 10 to about 200 mM or about 50 to about 150 mM. In yet another embodiment, the concentration of ammonium phosphate is about 100 to about 600 mM, about 150 to about 500 mM or about 200 to about 400 mM. In yet another embodiment, the concentration of dextran sulfate is about 0.1 to 20 mM or about 1 to 10 mM.

In accordance with the invention, the liposome encapsulating a trapping agent can be prepared by any of the techniques now known or subsequently developed. For example, the MLV liposomes can be directly formed by a hydrated lipid film, spray-dried powder or lyophilized cake of selected lipid compositions with trapping agent; the SUV liposomes and LUV liposomes can be sized from MLV liposomes by sonication, homogenization, microfluidization or extrusion.

Pharmaceutical Compositions

The present invention is directed to a sustained release pharmaceutical composition, comprising (a) at least one liposome comprising a bilayer membrane; (b) a trapping agent; and (c) an immunomodulating agent, wherein the bilayer membrane comprises at least one lipid and the molar ratio of the immunomodulating agent to the lipid is above or equal to about 0.2. In some embodiments, the molar ratio of the therapeutic agent to the lipid is above or equal to about 0.2 to less than about 20, less than about 15, less about 10, less than about 5, less than about 4, less than about 3 or less than about 2.

In one embodiment, the sustained release pharmaceutical composition further comprises at least one pharmaceutically acceptable excipient, diluent, vehicle, carrier, medium for the active ingredient, a preservative, cryoprotectant or a combination thereof. In one exemplary embodiment, the weight percent of the bilayer membrane in the pharmaceutical composition is about 0.1-12%; the weight percent of the trapping agent in the pharmaceutical composition is about 0.1-10%; and the weight percent of the pharmaceutically acceptable excipient (such as sucrose, histidine, sodium chloride and ultrapure water), diluent, vehicle, carrier, medium for the active ingredient, a preservative, cryoprotectant or a combination thereof in the pharmaceutical composition is about 80.0-99.9%.

In certain embodiments, the therapeutic agent for treating an auto-immune disease or the immunomodulating agent is a sphingosine-1-phosphate (S1P) receptor agonist. In certain embodiments, the immunomodulating agent is etrasimod, fingolimod, laquinimod, ozanimod, ponesimod, siponimod and a combination thereof. The sustained release profile of the pharmaceutical composition prolongs the half-life, the therapeutic concentration and the duration of action of the immunomodulating agent, and hence, sustains the therapeutic efficacy and reduces the dosage and/or dosing frequency of the immunomodulating agent.

In one aspect, the sustained release profile of the pharmaceutical composition is due to a high drug encapsulation efficiency. The encapsulation efficiency of these formulations is at least 50%, 55%, 60%, 65%, 70%, 75%, 80%, 90% or 95%.

In another aspect, sustained release profile of the pharmaceutical composition is due to the higher drug to lipid molar ratio. In an exemplary embodiment, the molar ratio of the immunomodulating agent to the one or more lipids is above or equal to about 0.20, 0.21, 0.22, 0.23, 0.24, 0.25, 0.26, 0.27, 0.28, 0.29, 0.3, 0.31, 0.32, 0.33, 0.34 or 0.35 to less than about 20, 15, 10, 5 or 2, alternatively from 0.2 to 20, from 0.2 to 15, from 0.2 to 10, from 0.2 to 5, from 0.2 to 2, from 0.3 to 20, from 0.3 to 15, from 0.3 to 10, from 0.3 to 5 or from 0.2 to 2.

In yet another aspect, the half-life of the immunomodulating agent is extended by at least 2-fold compared to that of the free immunomodulating agent.

The pharmaceutical composition is formulated to be suitable for injection, such as subcutaneous, subdermal, intradermal or intramuscular route.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, any existing medical conditions, and on the discretion of medical professionals.

In one embodiment, the pharmaceutical compositions disclosed herein display a significant extended-release profile of the immunomodulating agent. For example, the pharmaceutical composition of the present invention extended the half-life of fingolimod to 95.5 hours in rats via preferred subcutaneous administration route (as disclosed in Example 5) compared to the FDA approved fingolimod formulation preferred oral administration route (21.0 hours in rats, GILENYA® New Drug Application submitted package, Novartis Pharmaceuticals, Application No.: 22-527). These pharmaceutical compositions are developed to reduce the dosing frequency of fingolimod.

The present invention also provides methods for treating an auto-immune disease, comprising the steps of administering an effective amount of the pharmaceutical composition described herein to a subject in need thereof.

EXAMPLES

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated.

Example 1

Preparation of Liposomal Fingolimod Formulation

Empty liposomes were prepared by a lipid film hydration-extrusion method. HSPC, cholesterol, and DSPE-PEG2000 (mole percent 59.5/39.6/0.9) were dissolved in chloroform and a thin lipid film was formed by removing the organic solvent under vacuum in a rotary evaporator. The dry lipid film was hydrated in 300 mM ammonium sulfate at 60° C. for 30 min and the empty liposomes were formed with ammonium sulfate encapsulated in the aqueous core. After six freeze-thaw cycles between liquid nitrogen and water at 60° C., the empty liposomes were subsequently extruded ten times through polycarbonate filter membranes with a pore size of 0.2 μm. Unencapsulated ammonium sulfate was removed by dialysis against a 9.4% sucrose solution.

A reaction mixture containing 7.8 mg/mL of fingolimod hydrochloride (MedChem Express), 20.7 mM of lipids of empty liposomes and 50 mM histidine buffer (pH 7) was incubated at 60° C. for 15 min. The unencapsulated fingolimod hydrochloride was separated by a Sephadex™ G-50 Fine gel (GE Healthcare) or dialysis bag (Spectrum Labs) against a 9.4% sucrose solution to obtain the liposomal fingolimod formulation. The concentrations of the encapsulated fingolimod hydrochloride and the lipid of the liposomal fingolimod formulation were measured using an ultraviolet/visible (UV/Vis) spectrophotometer to calculate the drug to lipid molar ratio (D/L) of the liposomal fingolimod formulation.

The encapsulation efficiency was calculated by the drug to lipid molar ratio (D/L) of the fingolimod hydrochloride encapsulated liposomes compared to the nominal D/L of reaction mixture, which was calculated by dividing the concentration of fingolimod hydrochloride by the lipid concentration of empty liposome. The particle size distribution was measured by a dynamic light scattering instrument (Zetasizer Nano-ZS90, Malvern).

Using 300 mM ammonium sulfate as a trapping agent, the liposomal fingolimod formulation has a final D/L of 1.1 and an encapsulation efficiency of 100%. The mean diameter of the liposomes was 162 nm.

Example 2

Preparation of Liposomal Ozanimod Formulation

Empty liposomes were prepared by a lipid film hydration-extrusion method. HSPC, cholesterol, and DPPG (mole percent 59.5/39.6/0.9) were dissolved in chloroform and a thin lipid film was formed by removing the organic solvent under vacuum in a rotary evaporator. The dry lipid film was hydrated in 300 mM ammonium sulfate at 60° C. for 30 min and the empty liposomes were formed with ammonium sulfate encapsulated in the aqueous core. After six freeze-thaw cycles between liquid nitrogen and water at 60° C., the empty liposomes were subsequently extruded ten times through polycarbonate filter membranes with a pore size of 0.2 μm. Unencapsulated ammonium sulfate was removed by dialysis against a 9.4% sucrose solution.

A reaction mixture containing 7.2 mg/mL of ozanimod (DC Chemicals), 20.6 mM of lipids of empty liposomes and 50 mM histidine buffer (pH 6.5) was incubated at 60° C. for 15 min. The unencapsulated ozanimod was separated by a Sephadex™ G-50 Fine gel (GE Healthcare) or dialysis bag (Spectrum Labs) against a 9.4% sucrose solution to obtain the liposomal ozanimod formulation. The concentrations of the encapsulated ozanimod and the lipid of the liposomal ozanimod formulation were measured using an ultraviolet/visible (UV/Vis) spectrophotometer to calculate the drug to lipid molar ratio (D/L) of the liposomal ozanimod formulation.

The encapsulation efficiency was calculated by the drug to lipid molar ratio (D/L) of the ozanimod encapsulated liposomes compared to the nominal D/L of reaction mixture, which was calculated by dividing the concentration of ozanimod by the lipid concentration of empty liposome. The particle size distribution was measured by a dynamic light scattering instrument (Zetasizer Nano-ZS90, Malvern).

Using 300 mM ammonium sulfate as a trapping agent, the liposomal ozanimod formulation has a final D/L of 0.87 and an encapsulation efficiency of around 100%. The mean diameter of the liposomes was 186.7 nm.

Example 3

The Effect of Different Trapping Agents on Drug Loading Profile

The liposome formulations were prepared according to Example 1, with the following trapping agents: (1) 75 mM of triethylammonium sucrose octasulfate, (2) 300 mM of ammonium sulfate, (3) 200 mM ammonium phosphate and (4) 7.0 mM of dextran sulfate. Table 1 shows the effect of different trapping agents on drug loading.

TABLE 1

The drug loading profile of different trapping agents

| Bilayer Membranes (mole percent) | Compound | Trapping Agent | Purified D/L (mole/mole) | Encapsulation Efficiency (%) | Average Particle Size (nm) |
|---|---|---|---|---|---|
| HSPC/cholesterol/DSPE-PEG2000 (59.5/39.6/0.9) | Fingolimod HCl | 1 | 1.28 | 100 | 288.0 |
| HSPC/cholesterol/DSPE-PEG2000 (59.5/39.6/0.9) | Fingolimod HCl | 2 | 1.11 | 100 | 162.1 |
| DMPC/cholesterol/DSPE-PEG2000 (59.5/40/0.5) | Fingohmod HCl | 2 | 1.13 | 100 | 154.5 |
| HSPC/cholesterol/DPPG (59.5/39.6/0.9) | Fingolimod HCl | 2 | 1.01 | 100 | 191.4 |
| DPPC/cholesterol/DSPE-PEG2000 (55.9/38.7/5.4) | Fingolimod HCl | 3 | 0.88 | 99 | 143.1 |
| HSPC/cholesterol (60/40) | Ozanimod | 1 | 0.49 | 100 | 215.2 |
| HSPC/cholesterol/DPPG (59.5/39.6/0.9) | Ozanimod | 2 | 0.87 | 100 | 186.7 |
| DSPC/cholesterol/DSPE-PEG2000 (59.5/39.6/0.9) | Ozanimod | 4 | 0.35 | 79 | 364.2 |

Example 4

Prolonged Release Profile of Liposomal Fingolimod

To setup an in vitro release system, 0.5 mL of liposomal fingolimod formulation prepared according to Example 1 and 0.5 mL of free fingolimod hydrochloride were each mixed with 0.5 mL of fetal bovine serum. The free fingolimod/serum mixture and liposomal fingolimod/serum mixture were placed in separate dialysis bags (Spectra/Pro®6 dialysis membrane, MWCO 50 kDa, Spectrum Labs) and both ends of the dialysis bags were sealed. Each dialysis bag was immersed in 15 mL PBS at pH 7.4, containing 0.06N HCl, in a 50-mL centrifuge tube and incubated at 37±1° C. water bath. At designated time points after incubation (1, 2, 4, 8 and 24 hours), 0.5 mL aliquot from the 15-mL PBS was sampled and 0.5 mL of fresh PBS was added to replenish the sampling aliquot each time. Drug concentrations of the sampling aliquots at each time point were analyzed using HPLC to create the in vitro release profile of the tested formulations.

As demonstrated in FIG. 1, almost 80 percent of free fingolimod was released through the dialysis bag within 4 hours. In contrast, the release rate of the liposomal fingolimod formulation through the dialysis bag over 24 hours (<10%) was lower than that of the free drug (>80%). The extended release profile of the liposomal fingolimod formulation of the present invention demonstrates the potential of the liposomal fingolimod formulation as a sustained drug delivery system.

Example 5

Pharmacokinetics (PK) Study of Liposomal Fingolimod

An in vivo PK evaluation of the liposomal fingolimod formulation was performed using 7- to 8-week-old female Sprague-Dawley rats. The rats were housed in a holding room which operated on a 12-hr light/12-hr dark circadian cycle with free access to water and food.

The rats were divided into three groups (n=4 in each group), one group received intravenous (IV) injection of 5 mg/Kg of free fingolimod hydrochloride, prepared by dissolving the fingolimod hydrochloride in a 9.4% sucrose solution containing 5% dimethyl sulfoxide with a final concentration of 2.00 mg/mL. The second group received intravenous (IV) injection of 5 mg/Kg of liposomal fingolimod formulation prepared according to Example 1. The third group received subcutaneous (SC) injection of 5 mg/Kg of liposomal fingolimod formulation prepared according to Example 1. Blood samples were collected at 5, 15 min, 1, 2, 4, 8, 24, 48, 72, and 96 hours post-injection. Plasma samples were obtained by centrifugation, kept frozen at -80° C. and analyzed using a noncompartmental analysis model in PKSolver (Comput. Methods Programs Biomed. 2010; 99(3):306-314). The PK parameters of the three fingolimod formulations are summarized in Table 2.

Table 2 shows the half-life ($t_{1/2}$) of fingolimod in the IV liposomal fingolimod group was similar to that of the IV free fingolimod group. IV administered free fingolimod and liposomal fingolimod were eliminated from the circulation after about 70 hours post IV administration, approximately 5 half-lives for both fingolimod forms. The $C_{max}$ for the SC liposomal fingolimod group was less than the $C_{max}$ observed for either IV administered free fingolimod and liposomal fingolimod, and the half-life ($t_{1/2}$) of subcutaneous administered liposomal fingolimod was significantly longer compared to that of IV administered free fingolimod and liposomal fingolimod. The ratio of area under the measured curve ($AUC_{0-t}$) to the extrapolated area under the curve ($AUC_{0-inf}$) indicates that 39.9% of fingolimod was released from the liposomal fingolimod formulation 96 hours post-subcutaneous injection whereas the $AUC_{0-t}/AUC_{0-inf}$ ratio of the intravenous injected free fingolimod was approximately 100% 96 hours post-injection.

Table 2 further illustrates the dose normalized $C_{max}$ ($C_{max}/D$) of SC injected liposomal fingolimod formulation of the present invention is 4.8 (ng/mL)/(mg/Kg), which is significantly lower compared to that of the FDA approved orally administered fingolimod (ranging from 20.4 to 30 (ng/mL)/(mg/Kg)). Likewise, the $t_{1/2}$ of SC injected liposomal fingolimod formulation of the present invention is 95.5 hours, which is significantly longer compared to that of the FDA approved orally administered fingolimod (13.6 to 25.1 hours in rats). The subcutaneous administered liposomal fingolimod formulation of the present invention has a $C_{max}/D$ that is one-sixth (⅙) to one quarter (¼) of that of the FDA approved fingolimod formulation while the $t_{1/2}$ is 3.8- to 7.0-times longer than that of the FDA approved fingolimod formulation.

TABLE 2

PK parameters derived from rats after a single SC injection of liposomal
fingolimod formulation or a single orally administered FDA approved fingolimod formulation

| Parameters | Unit | Liposomal Fingolimod Formulation SC | Fingolimod Formulation[†] Oral | | |
|---|---|---|---|---|---|
| Dosage | mg/Kg | 5 | 0.1 | 1.0 | 3.0 |
| $t_{1/2}$ | h | 95.5 | 13.6 | 25.1 | 15.6 |
| $C_{max}$ | ng/mL | 24.0 | 3 | 20 | 70.8 |
| $C_{max}/D$ | (ng/mL)/(mg/Kg) | 4.8 | 30 | 20.4 | 23.6 |
| $AUC_{0-t}$ | h × ng/mL | 1220 | 63 | 627 | 573 |
| $AUC_{0-t}/D$ | (h × ng/mL)/(mg/Kg) | 244 | 631 | 627 | 191 |
| $AUC_{0-inf}$ | h × ng/mL | 3060 | — | — | — |

$C_{max}/D$, dose-normalized $C_{max}$; $AUC_{0-t}/D$ dose-normalized $AUC_{0-t}$.
[†]Data were derived from GILENYA ® New Drug Application submitted package, Novartis Pharmaceuticals, Application No.: 22-527.

Table 3 illustrates the PK parameters of the IV injected liposomal fingolimod formulation of the present invention and the IV injected liposomal fingolimod formulation from Mao et al. (Nanomed. 2014; 10(2): 393-400). The $C_{max}$ and $AUC_{0-inf}$ values (ratio of liposomal drug to free drug) of the present invention are about 4-times higher than those of Mao et al. In addition, the apparent volume of distribution ($V_d$) and clearance (CL) values (ratio of liposomal drug to free drug) of the present invention are significantly lower than those in Mao et al. These results demonstrate that the liposomal fingolimod formulation of the present invention sustains the drug release in circulation compared to the liposomal formulation of Mao et al.

TABLE 3

PK parameters derived from rats and mice after a single IV injection of the
liposomal fingolimod formulation of the present invention and of Mao et al.

| Parameters | IV liposomal fingolimod of present invention | IV liposomal fingolimod of Mao et al.[§] |
|---|---|---|
| Dosage (mg/Kg) | 5 | 5 |
| Ratio of Liposomal Fingolimod $C_{max}$ to Fingolimod $C_{max}$ | 8.4 | 2.2 |
| Ratio of Liposomal Fingolimod $AUC_{0-inf}$ to Fingolimod $AUC_{0-inf}$ | 12.9 | 3.3 |
| Ratio of Liposomal Fingolimod $V_d$ to Fingolimod $V_d$ | 0.05 | 0.44 |
| Ratio of Liposomal Fingolimod CL to Fingolimod CL | 0.08 | 0.30 |

[§]Data were derived from Nanomed. 2014; 10(2): 393-400.

The invention claimed is:
1. A pharmaceutical composition, comprising
   (a) at least one liposome comprising a bilayer membrane, wherein the bilayer membrane comprises a mixture of about 45 to about 80 mole percent of a first lipid that is selected from the group consisting of 1,2-distearoyl-sn-glycero-3-phosphocholine (HSPC), 1,2-dipalmitoyl-sn-glycero-3-phosphocholine (DPPC), 1,2-dimyristoyl-sn-glycero-3-phosphocholine (DMPC) and any combination thereof, about 20 to about 55 mole percent of cholesterol and 0.1-10 mole percent of a second lipid that is selected from the group consisting of N-(carbonyl-methoxypolyethyleneglycol)-1,2-distearoyl-sn-glycero-3-phosphoethanolamine (PEG-DSPE), 1,2-dipalmitoyl-sn-glycero-3-phosphocholine (DPPG) and any combination thereof;
   (b) a trapping agent selected from the group consisting of triethylammonium sucrose octasulfate, ammonium sulfate, ammonium phosphate, and any combination thereof; and
   (c) a sphingosine-1-phosphate (S1P) receptor agonist that is fingolimod or ozanimod,
   wherein the molar ratio of the sphingosine-1-phosphate (S1P) receptor agonist to the lipid is higher than about 0.87 and the S1P receptor agonist is encapsulated in the liposome with an encapsulation efficiency higher than about 90%,
   wherein when the S1P receptor agonist is fingolimod, the trapping agent is triethylammonium sucrose octasulfate, ammonium sulfate or ammonium phosphate, when the S1P receptor agonist is ozanimod, the trapping agent is ammonium sulfate.

2. The pharmaceutical composition of claim 1, wherein the mean particle size of the liposome is from about 50 nm to 20 μm.

3. The pharmaceutical composition of claim 1, wherein the mole percentage of first lipid: second lipid: cholesterol in the bilayer membrane is 45-70%: 0.1-10%: 25-45%.

4. The pharmaceutical composition of claim 1, wherein the concentration of triethylammonium sucrose octasulfate is about 10 to 200 mM.

5. The pharmaceutical composition of claim 1, wherein the concentration of ammonium sulfate is about 100 to 600 mM.

6. The pharmaceutical composition of claim 1, wherein the concentration of ammonium phosphate is about 100 to 600 mM.

7. A pharmaceutical composition, comprising
   (a) at least one liposome comprising a bilayer membrane, wherein the bilayer membrane comprises a mixture of about 45 to about 80 mole percent of a first lipid that is phosphatidylcholine (PC), 1,2-distearoyl-sn-glycero-3-phosphocholine (HSPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1-palmitoyl-2-stearoyl-sn-glycero-3-phosphocholine (PSPC) and any combination thereof, about 20 to about 55 mole percent of cholesterol and 0.1-10 mole percent of a second lipid that is phosphatidylethanolamine (PE) or PEG-DSPE;

(b) a trapping agent that is ammonium sulfate; and (c) fingolimod, wherein less than 10% of fingolimod is released into a dialysis bag over 24 hours.

8. The pharmaceutical composition of claim 7, wherein the first phospholipid is HSPC and the second lipid is PEG-DSPE.

\* \* \* \* \*